US00PP14286P29

(12) United States Plant Patent
Verwer

(10) Patent No.: US PP14,286 P2
(45) Date of Patent: Nov. 11, 2003

(54) DAHLIA PLANT NAMED 'MELODY MAMBO'

(50) Latin Name: *Dahlia hybrida*
Varietal Denomination: Melody Mambo

(75) Inventor: Aad W. M. Verwer, Lisse (NL)

(73) Assignee: Verwer Dahlias B.V., Lisse (NL)

( * ) Notice: Subject to any disclaimer, the term of this patent is extended or adjusted under 35 U.S.C. 154(b) by 0 days.

(21) Appl. No.: 10/223,516

(22) Filed: Aug. 19, 2002

(51) Int. Cl.[7] ..... A01H 5/00
(52) U.S. Cl. ..... Plt./321
(58) Field of Search ..... Plt./321

(56) References Cited

PUBLICATIONS

UPOV–ROM GTITM, Plant Variety Database, 2003/01, GTI Jouve Retrieval Software, Citation for Dahlia 'Melody Mambo'.*

* cited by examiner

*Primary Examiner*—Bruce R. Campell
*Assistant Examiner*—June Hwu
(74) *Attorney, Agent, or Firm*—C. A. Whealy

(57) ABSTRACT

A new and distinct cultivar of Dahlia plant named 'Melody Mambo', characterized by its upright and outwardly spreading plant habit; freely branching growth habit; early and freely flowering habit; decorative inflorescence form; large inflorescences with dark red-colored ray florets; and good postproduction longevity and garden performance.

1 Drawing Sheet

Botanical classification/cultivar designation: *Dahlia hybrida* cultivar Melody Mambo.

BACKGROUND OF THE INVENTION

The present Invention relates to a new and distinct cultivar of Dahlia plant, botanically known as Dahlia hybrida and hereinafter referred to by the name 'Melody Mambo'.

The new Dahlia is a product of a planned breeding program conducted by the Inventor in Lisse, The Netherlands. The objective of the breeding program is to create new potted Dahlia cultivars with compact plant habit, freely branching growth habit, early and freely flowering habit, decorative inflorescence form, attractive ray floret coloration, and good postproduction longevity and garden performance.

The new Dahlia originated from a cross pollination made by the Inventor during the summer of 1997 of the *Dahlia hybrida* Gallery Art Deco, disclosed in U.S. Plant Pat. No. 10,525, as the female, or seed, parent with the *Dahlia hybrida* cultivar Melody Bolero, disclosed in U.S. Plant patent application Ser. No. 09/552,707, as the male, or pollen, parent. The new Dahlia was discovered and selected by the Inventor as a single flowering plant within the progeny of the stated cross pollination grown in a controlled environment in Lisse, The Netherlands, in the summer of 1998.

Asexual reproduction of the new Dahlia by cuttings was first conducted in Lisse, The Netherlands in February, 1999. Asexual reproduction by cuttings has shown that the unique features of this new Dahlia are stable and reproduced true to type in successive generations.

SUMMARY OF THE INVENTION

The cultivar Melody Mambo has not been observed under all possible environmental conditions. The phenotype may vary somewhat with variations in environment such as temperature and light intensity without, however, any variance in genotype.

The following traits have been repeatedly observed and are determined to be the unique characteristics of 'Melody Mambo'. These characteristics in combination distinguish 'Melody Mambo' as a new and distinct Dahlia cultivar:

1. Upright and outwardly spreading plant habit.
2. Freely branching growth habit.
3. Early and freely flowering habit.
4. Decorative inflorescence form.
5. Large inflorescences with dark red-colored ray florets.
6. Good postproduction longevity and garden performance.

Plants of the new Dahlia differ primarily from plants of the female parent, the cultivar Gallery Art Deco in leaf color, inflorescence form and ray floret color. Plants of the new Dahlia differ primarily from plants of the male parent, the cultivar Melody Bolero in plant size, leaf color, inflorescence form and ray floret color.

Plants of the new Dahlia can be compared to plants of the cultivar Heatwave, not patented. In side-by-side comparisons conducted in Lisse, The Netherlands, plants of the new Dahlia differed from plants of the cultivar Heatwave in the following characteristics:

1. Plants of the new Dahlia were more compact and more freely branching than plants of the cultivar Heatwave.
2. Plants of the new Dahlia flowered earlier than plants of the cultivar Heatwave.
3. Ray floret color of plants of the new Dahlia was darker red than ray floret color of plants of the cultivar Heatwave.

BRIEF DESCRIPTION OF THE PHOTOGRAPH

The accompanying colored photograph illustrates the overall appearance of the new Dahlia showing the colors as true as it is reasonably possible to obtain in colored reproductions of this type. Colors in the photograph may differ from the color values cited in the detailed botanical description which accurately describe the colors of the new Dahlia.

The photograph comprises a side perspective view of typical flowering plants of 'Melody Mambo'.

DETAILED BOTANICAL DESCRIPTION

In the following description, color references are made to The Royal Horticultural Society Colour Chart, 1995 Edition, except where general terms of ordinary dictionary significance are used. The aforementioned photograph and the following observations and measurements describe plants grown and flowered during the summer and early autumn of 2001 in Lisse, The Netherlands, in an outdoor nursery and under conditions which approximate those generally used in commercial production. During the production of the plants, day temperatures ranged between 15 and 30° C. and night temperatures ranged between 10 and 20° C. Plants were pinched one time about three weeks after planting rooted cuttings. Plants were about four months old when the photographs and the description were taken.

Botanical classification: *Dahlia hybrida* cultivar Melody Mambo.

Parentage:

*Female, or seed, parent.*—*Dahlia hybrida* cultivar Gallery Art Deco, disclosed in U.S. Plant Pat. No. 10,525.

*Male, or pollen, parent.*—*Dahlia hybrida* cultivar Melody Bolero, disclosed in U.S. Plant patent application Ser. No. 09/552,707.

Propagation:

*Type.*—By vegetative cuttings.

*Time to initiate roots.*—Summer and winter: About 5 days at 17° C.

*Time to produce a rooted young plant.*—Summer: About 14 days at 17° C. Winter: About 17 days at 17° C.

*Root description.*—Fine, fibrous and well-branched; older roots, fleshy.

*Tuber description.*—Shape: Fusiform. Clump diameter: About 25 cm. Color: Close to 199C.

Plant description:

*Appearance.*—Perennial decorative-type potted Dahlia. Upright and outwardly spreading plant habit. Freely branching habit, about eight lateral branches develop after pinching; dense and full plants. Vigorous.

*Plant height.*—About 55 cm.

*Plant diameter.*—About 35 cm.

*Lateral branch description.*—Length: About 34 cm. Diameter: Towards base: About 8 mm. Towards apex: About 3 mm. Internode length: About 2 to 8 cm. Strength: Strong. Texture: Glabrous, smooth. Color: 146D.

*Foliage description.*—Arrangement: Leaves opposite; leaves may be single or compound with three or five leaflets. Shape: Ovate. Apex: Acute. Base: Attenuate. Margin: Irregularly serrate; sinuses divergent. Length: Single leaves: About 8 cm. Compound leaves with three leaflets: About 14 cm. Compound leaves with five leaflets: About 19 cm. Width: Single leaves: About 4.3 cm. Compound leaves with three leaflets: About 15 cm. Compound leaves with five leaflets: About 14 cm. Venation pattern: Pinnate. Texture, upper and lower surfaces: Smooth, glabrous. Color: Young foliage, upper surface: 137A. Young foliage, lower surface: 191B. Fully expanded foliage, upper surface: Darker than 137A. Fully expanded foliage, lower surface: 191A. Venation, upper surface: 138B. Venation, lower surface: 144B. Petiole length: About 4 cm. Petiole diameter: About 2.3 mm. Petiole color: Upper surface: 144A. Lower surface: 144C.

Inflorescence description:

*Appearance.*—Decorative inflorescence form; inflorescences roughly hemispherical in profile. Inflorescences borne on terminals, arising from leaf axils, positioned above the foliage. Ray and disc florets develop acropetally on the receptacle. Inflorescences not fragrant. Inflorescences persistent.

*Flowering response.*—Flowering recurrent to continuous during the summer and autumn in The Netherlands. Plants start flowering about 56 days after planting.

*Postproduction longevity.*—On the plant, inflorescences maintain good color and substance for about 25 days in an outdoor environment. As cut flowers, inflorescences maintain good color and substance for about five days in an indoor environment.

*Quantity of inflorescences per flowering stem.*—About five inflorescences; about 48 inflorescences per plant develop during the growing season.

*Inflorescence size.*—Diameter: About 11 cm. Depth (height): About 5.5 cm. Diameter of disc: About 3.4 cm. Receptacle diameter: About 1.6 cm. Receptacle height: About 1.2 cm.

*Inflorescence buds.*—Length: About 1.2 cm. Diameter: About 1.7 cm. Shape: Oblate. Color: 153B.

*Ray florets.*—Length, fully developed: About 3.7 cm. Width, fully developed: About 1.4 cm. Orientation: Initially upright, outer florets perpendicular to the peduncle to somewhat reflexed. Shape: Ovate. Aspect: Longitudinal axis concave. Apex: Acute. Base: Attenuate. Margin: Entire. Texture, upper and lower surfaces: Smooth, glabrous. Number of ray florets per inflorescence: About 120 arranged in about 15 rows. Venation pattern: Parallel. Color: When opening, upper surface: Darker than 187A. When opening, lower surface: 187A. Fully opened, upper surface: Towards the apex, 46A; towards the base, 46B. Fully opened, lower surface: Towards the apex, 187C; towards the base, 46B.

*Disc florets.*—Number of disc florets per inflorescence: About 38. Shape: Tubular, elongated. Apex: Five-pointed. Base: Attenuate. Length: About 8 mm. Width: At the apex, about 0.8 mm; at the base, about 0.6 mm. Color: Immature: 17B. Mature: Apex: 15A. Mid-section: 17A. Base: 1C.

*Phyllaries.*—Quantity: One whorl with about eight phyllaries. Shape: Ovate. Apex: Acute. Base: Attenuate. Margin: Entire. Length: About 9 mm. Width: About 3 mm. Texture, upper and lower surfaces: Smooth, glabrous; leathery. Color, upper and lower surfaces: 138A.

*Peduncles.*—Length: About 12 cm. Diameter: About 1.8 mm. Angle: About 40° from vertical. Strength: Strong. Texture: Glabrous, smooth. Color: 144B.

*Reproductive organs.*—Androecium: Present on disc florets only. Stamen quantity: About five per floret. Anther shape: Linear. Anther length: About 3 mm. Anther color: 17A. Pollen amount: Scarce. Pollen color: 21A. Gynoecium: Present on ray and disc florets. Pistil quantity: One per floret. Pistil length: About 2 mm. Stigma shape: Lanceolate. Stigma color: Close to 13B. Style length: About 2 mm. Style color: 150C. Ovary color: 9C.

*Seeds/fruits.*—Seed and fruit development has not been observed.

Disease/pest resistance: Resistance to pathogens and pests common to Dahlias has not been observed on plants grown under commercial greenhouse or outdoor conditions.

Weather tolerance: Plants of the new Dahlia have been observed to be very tolerant to wind, rain and full sun conditions. Plants of the new Dahlia have been observed to be tolerant temperatures from 0 to 40° C.

It is claimed:

1. A new and distinct cultivar of Dahlia plant named 'Melody Mambo', as illustrated and described.

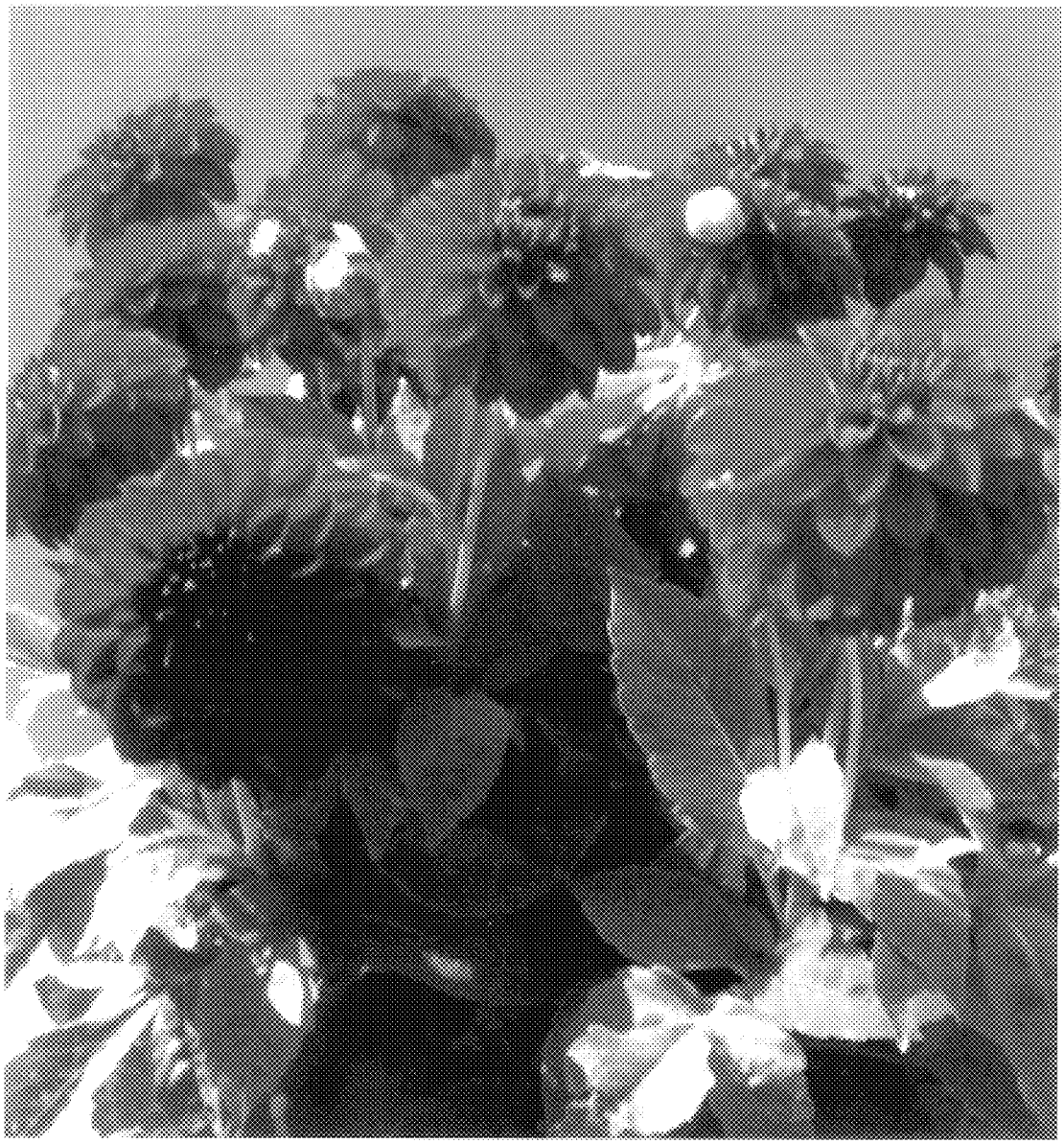

* * * * *